United States Patent
Ge et al.

(10) Patent No.: US 10,464,859 B2
(45) Date of Patent: *Nov. 5, 2019

(54) METHOD FOR PREPARING AROMATIC HYDROCARBON WITH CARBON DIOXIDE HYDROGENATION

(71) Applicant: DALIAN INSTITUTE OF CHEMICAL PHYSICS, CHINESE ACADEMY OF SCIENCES, Dalian (CN)

(72) Inventors: Qingjie Ge, Dalian (CN); Jian Wei, Dalian (CN); Hengyong Xu, Dalian (CN)

(73) Assignee: DALIAN INSTITUTE OF CHEMICAL PHYSICS, CHINESE ACADEMY OF SCIENCES, Dalian (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/085,397

(22) PCT Filed: Jul. 25, 2017

(86) PCT No.: PCT/CN2017/094192
§ 371 (c)(1),
(2) Date: Sep. 14, 2018

(87) PCT Pub. No.: WO2018/049919
PCT Pub. Date: Mar. 22, 2018

(65) Prior Publication Data
US 2019/0071374 A1    Mar. 7, 2019

(30) Foreign Application Priority Data

Sep. 19, 2016 (CN) .......................... 2016 1 0832357

(51) Int. Cl.
| | | |
|---|---|---|
| *C10G 2/00* | (2006.01) | |
| *C07C 1/12* | (2006.01) | |
| *B01J 29/46* | (2006.01) | |
| *C07C 15/06* | (2006.01) | |
| *C07C 15/073* | (2006.01) | |
| *B01J 29/40* | (2006.01) | |
| *B01J 29/70* | (2006.01) | |
| *B01J 29/76* | (2006.01) | |
| *B01J 37/04* | (2006.01) | |
| *B01J 37/06* | (2006.01) | |
| *B01J 23/745* | (2006.01) | |
| *B01J 37/00* | (2006.01) | |

(52) U.S. Cl.
CPC .............. *C07C 1/12* (2013.01); *B01J 29/405* (2013.01); *B01J 29/46* (2013.01); *B01J 29/7088* (2013.01); *B01J 29/7676* (2013.01); *B01J 37/04* (2013.01); *B01J 37/06* (2013.01); *C07C 15/06* (2013.01); *C07C 15/073* (2013.01); *C10G 2/50* (2013.01); *B01J 23/745* (2013.01); *B01J 37/009* (2013.01); *C07C 2523/745* (2013.01); *C07C 2529/46* (2013.01); *C07C 2529/48* (2013.01)

(58) Field of Classification Search
None
See application file for complete search history.

(56) References Cited

U.S. PATENT DOCUMENTS 5,865,988 A    2/1999    Collins et al.

FOREIGN PATENT DOCUMENTS

| CN | 101352689 A | 1/2009 |
|---|---|---|
| CN | 102091618 A | 6/2011 |
| CN | 102941098 A | 2/2013 |
| CN | 104368378 A | 2/2015 |
| CN | 104496743 A | 4/2015 |

(Continued)

OTHER PUBLICATIONS

Wei, J. et al. "Directly converting CO2 into a gasoline fuel" Nature Communication, Published May 2, 2017 (Year: 2017).*
Fujiwara, M. et al. "Change of catalytic properties of Fe—ZnO/zeolite composite catalyst in the hydrogenation of carbon dioxide" Applied Catalysis A: General 154 (1997) 87-101 (Year: 1997).*
DE-102013022290-A1, translation, Mar. 26, 2015, pp. 1-16 (Year: 2015).*
Riedel, T. et al. "Comparative study of Fischer-Tropsch synthesis with H2/CO and H2/CO2 syngas using Fe- and Co-based catalysts" Applied Catalysis A: General 186 (1999) 201-213 (Year: 1999).*

(Continued)

*Primary Examiner* — Medhanit W Bahta
(74) *Attorney, Agent, or Firm* — Enshan Hong; VLP Law Group LLP

(57) ABSTRACT

A method for preparing aromatic hydrocarbons with carbon dioxide hydrogenation, comprising: directly converting a mixed gas consisting of carbon dioxide and hydrogen with the catalysis of a composite catalyst under reaction conditions of a temperature of 250-450° C., a pressure of 0.01-10.0 MPa, a feedstock gas hourly space velocity of 500-50000 mL/(h·$g_{cat}$) and a $H_2/CO_2$ molar ratio of 0.5-8.0, to produce aromatic hydrocarbons. The composite catalyst is a mixture of a first component and a second component. The first component is an iron-based catalyst for making low-carbon olefin via carbon dioxide hydrogenation, and the second component is at least one of metal modified or non-modified molecular sieves which are mainly used for olefin aromatization. In the method, $CO_2$ conversion per pass may be above 33%, the hydrocarbon product selectivity may be controlled to be above 80%, the methane content is lower than 8%, $C_{5+}$ hydrocarbon content is higher than 65% and the proportion of the aromatic hydrocarbons in $C_{5+}$ hydrocarbons may be above 63%.

16 Claims, No Drawings

(56) References Cited

FOREIGN PATENT DOCUMENTS

CN           104624194 A     5/2015
DE       102013022290 A1 *   3/2015   ............ B01J 37/04

OTHER PUBLICATIONS

"Main sources of carbon dioxide emissions" Jun. 3, 2016 (Year: 2016).*
"Gasoline" from Chemical and Physical Information, 2019 (Year: 2019).*
Yisheng Tan et al., "Syntheses of Isobutane and Branched Higher Hydrocarbons from Carbon Dioxide and Hydrogen over Composite Catalysts", Ind. Eng. Chem. Res. 1999, 38, 3225-3229.
Masahiro Fujiwaraa et al., "CO2 hydrogenation for C2+ hydrocarbon synthesis over composite catalyst using surface modified HB zeolite", Applied Catalysis B: Environmental 179 (2015) 37-43.

\* cited by examiner

METHOD FOR PREPARING AROMATIC HYDROCARBON WITH CARBON DIOXIDE HYDROGENATION

RELATED APPLICATIONS

This is a U.S. national stage of international application No. PCT/CN2017/094192 filed on Jul. 25, 2017, which claims priority from China Patent Application No. 201610832357.5 filed on Sep. 19, 2016, the entire content of which is incorporated herein as reference.

TECHNICAL FIELD

The present invention relates to a production method of aromatic hydrocarbons, and particularly relates to a method for preparing aromatic hydrocarbons with carbon dioxide hydrogenation.

BACKGROUND OF THIS INVENTION

As an important basic chemical raw material, aromatic hydrocarbons are mainly used in the production of chemical products such as chemical fibers, plastics and rubber. With the rapid development of petrochemical and textile industries and the continuous development of textile industry, the global demand for the aromatic hydrocarbons is increasing with time. At present, industrial production of the aromatic hydrocarbons mainly comes from oil and coal. The way to take the oil as raw material includes reforming production of refineries, gasoline pyrolysis of ethylene plants and toluene disproportionation, and the way to take the coal as raw material mainly comes from coal coking. However, the reserves of fossil resources such as coal and oil are limited, so it is of great significance to develop the route to obtain the aromatic hydrocarbons from non-fossil resources. $CO_2$, as the cheapest and most abundant resource in the carbon family, is abundant on earth. With the continuous development of human society, the use amount of the fossil energy has increased sharply, and the content of $CO_2$ in the atmosphere has increased with time, which not only aggravates the greenhouse effect, but also causes a huge waste of carbon resources. The $CO_2$ captured in industrial waste gas or atmosphere is used for the production of hydrogen from renewable energy sources; and a circulation mode for preparing liquid hydrocarbon through $CO_2$ catalytic hydrogenation is conducted, which is of great significance to solving two new challenges of climate change and energy crisis in human society.

The research shows that the preparation of hydrocarbons by $CO_2$ hydrogenation usually takes two steps. First, $CO_2$ is subjected to reversed water gas shift reaction to produce CO, and then CO is subjected to Fischer-Tropsch synthesis to form the hydrocarbon compounds. In the traditional Fischer-Tropsch synthesis process of CO hydrogenation to produce hydrocarbons, the product selectivity is limited by the anderson-schulz-flory (ASF) rule. According to the ASF distribution, the maximum selectivity of C5-C11 hydrocarbons is only 45%. Unlike CO hydrogenation, because $CO_2$ is slow in absorption on a catalyst surface, in the $CO_2$ hydrogenation, C/H ratio on the catalyst surface is low. This phenomenon is conducive to the surface adsorption of species for hydrogenation and reducing the chain growth probability of products, thereby improving the methane selectivity. However, it makes it more difficult for $CO_2$ hydrogenation to prepare long-chain hydrocarbons. Therefore, at present, the target products researched in $CO_2$ hydrogenation are mainly methanol (such as CN201110006073.8) dimethyl ether (such as CN201410495290.1), methane (such as CN201210444697.2) and low-carbon olefin (such as CN201510102620.0) and other small molecular weight hydrocarbons or oxygen containing compounds, while there are few studies on the preparation of long chain hydrocarbons by $CO_2$ hydrogenation. Literature (Y. Tan et al. Ind. Eng. Chem. Res. 38(1999) 3225-3229) reports that when Fe—Zn—Zr/HZSM-5 composite catalyst is used and $CO_2$ conversion rate is about 19.5%, $C_{5+}$ hydrocarbon selectivity can reach 52%, but the selectivity of the side product CO can reach 57.4% and $C_{5+}$ yield is very low. Recently, M. Fujiwara, et al. (Appl. Catal. B: Environ 179 (2015) 37-43) has found that the Cu—Zn—Al methanol synthesizing catalyst is mixed with modified HB molecular sieve to obtain a composite catalyst, and $C_{2+}$ hydrocarbon can be obtained by $CO_2$ hydrogenation, but the selectivity of the side product CO is higher than 50%.

The efficiency of $CO_2$ hydrogenation to directly produce liquid hydrocarbons is low, and especially for aromatic hydrocarbons as part of liquid hydrocarbons, the efficiency is lower (the selectivity of the side product CO and the selectivity of methane are too high), which is also an important reason that there is no report about $CO_2$ hydrogenation to efficiently prepare the aromatic hydrocarbons. Therefore, how to find a technical route for efficient production of the aromatic hydrocarbons by $CO_2$ hydrogenation has become a great challenge in the field of $CO_2$ conversion and utilization.

SUMMARY OF THE INVENTION

The present invention aims to solve the technical problems of low selectivity of aromatic hydrocarbon, high selectivity of side products CO and methane, low $CO_2$ utilization rate and the like in the prior art, so as to provide a new method for preparing aromatic hydrocarbons with carbon dioxide hydrogenation.

The present invention provides a method for preparing aromatic hydrocarbon with carbon dioxide hydrogenation, comprising: directly converting a mixed gas, used as feedstock gas, consisting of carbon dioxide and hydrogen with the catalysis of a composite catalyst to produce aromatic hydrocarbons. The composite catalyst is a mixture of a first component and a second component, wherein the first component is a low-carbon olefin synthesis catalyst which is composed of iron-based carbon dioxide hydrogenation active component, and the second component is one or more than two of metal modified or non-modified molecular sieves which are mainly used for olefin aromatization. The mass ratio of the first component to the second component is 1:10-10:1, and preferably 1:3-3:1. The prepared aromatic hydrocarbon products mainly include high value added products such as toluene, ethybenzene, xylene, methyl ethylbenzene, trimethyl benzene, dimethyl ethybenzene, etc.

In the present invention, reaction conditions for preparing aromatic hydrocarbon with carbon dioxide hydrogenation are: a reaction temperature of 250-450° C., a reaction pressure of 0.01-10.0 MPa, an feedstock gas hourly space velocity of 500-50000 mL/(h·$g_{cat}$) and a $H_2/CO_2$ molar ratio in the feedstock gas of 0.5-8.0.

Main active components of the low-carbon olefin synthesis catalyst composed of iron-based carbon dioxide hydrogenation active component, preferably comprise one or more than two of Fe, FeO, $Fe_2O_3$ and $Fe_3O_4$ with good reverse water gas conversion function and olefin production function with CO hydrogenation, and preferably comprise Fe$_3$O$_4$; the auxiliary is added or not added; the auxiliary is an oxide; and the content of the auxiliary is 0-20% of the total mass of the iron-based catalyst. The auxiliary is one or more than two of K oxide, Na oxide, Cu oxide, Mn oxide, V oxide, Zr oxide, Zn oxide and Ce oxide; and the preferred content of the auxiliary in the catalyst is 0.5-10% of the total mass of the low-carbon olefin catalyst which is prepared by the iron-based carbon dioxide hydrogenation.

The molecular sieve means a molecular sieve containing ten-membered ring porous structure, preferably is one or more than two of ZSM-5, ZSM-22, ZSM-23 and MCM-22 molecular sieves, and most preferably is one or two of ZSM-5 and MCM-22 molecular sieves; the silica alumina ratio of the used molecular sieve is 20-200; metal used by a modified molecular sieve comprises one or more than two of Mo, Ga, Cr, La, Cu and Zn; and metallic elements are 0.1%-20% of the mass of the modified molecular sieve, and preferably 0.5%-10%.

The low-carbon olefin synthesis catalyst component composed of the iron-based CO$_2$ hydrogenation component can be prepared by one of the following three processes, and the Fe$_3$O$_4$ active component is used as an example to describe specific steps, but not used to limit the present invention.

A. the catalyst is prepared by a one-step synthesis method which comprises the following steps:

(1) mixing soluble Fe (II) salt and soluble Fe (III) salt to form a salt solution or mixing soluble Fe (II) salt, soluble Fe (III) salt and auxiliary salt to form a salt solution in accordance with a catalyst composition ratio, the concentration of Fe (III) in the salt solution being 0.02-0.8 mol/L; adding HCl solution with a concentration of 3-12.1 mol/L; regulating a pH value to 0-3, wherein the molar ratio of Fe(III) to Fe(II) in the salt solution is 2:(0.8-2.8);

the soluble Fe (II) salt and the soluble Fe (III) salt mean water-soluble salt compounds, and preferably are one or more than two of chlorid, nitrate and acetate; and the auxiliary salt is a water-soluble salt compound, and preferably are one or more than two of chlorid, nitrate and acetate;

(2) adding aqueous alkali to (1); gradually regulating the pH value of the solution to 0-3 until the alkaline pH value is 9-12; after completing dripping, ageing for 1-10 h, wherein the aqueous alkali means an alkali solution with an adjustable pH value, and preferably is one or more than two of NaOH, KOH, Na$_2$CO$_3$, NaHCO$_3$, K$_2$CO$_3$, KHCO$_3$, Na$_2$C$_2$O$_4$, K$_2$C$_2$O$_4$, RCOONa, RCOOK and ammonium hydroxide; the concentration of the aqueous alkali is 0.1-8 mol/L, wherein R refers to an organo-functional group and comprises C1-C20 alkyl, C1-C20 alkenyl or C6-C20 aryl, and preferably is methyl, ethyl or phenyl;

(3) after completing the reaction, separating deposited products from (2) through magnetic field absorption, centrifugal or sucking filtration method; adequately washing the deposited products with deionized water, drying, roasting or not roasting at a roasting temperature of 200-600° C. for a roasting time of 2-10 h, to prepare the iron-based catalyst containing the auxiliary;

B. or the catalyst is prepared by a one-step synthesis method which comprises the following steps:

(1) mixing soluble Fe (II) salt and soluble Fe (III) salt to form a salt solution to form a salt solution in accordance with a catalyst composition ratio, the concentration of Fe (III) in the salt solution being 0.02-0.8 mol/L; adding HCl solution with a concentration of 3-12.1 mol/L; regulating a pH value to 0-3, wherein the molar ratio of Fe(III) to Fe(II) in the salt solution is 2:(0.8-2.8);

(2) adding aqueous alkali containing Na or K in A method to (1); gradually regulating the pH value of the solution to 0-3 until the alkaline pH value is 9-12; after completing dripping, ageing for 1-10 h, wherein (3) after completing the reaction, separating deposited products from (2) through magnetic field absorption, centrifugal or sucking filtration method; washing the deposited products with deionized water; controlling the content of remaining Na or K in the catalyst by controlling washing times and water consumption per washing; drying, roasting or not roasting at a roasting temperature of 200-600° C. for a roasting time of 2-10 h, to prepare the iron-based catalyst containing the auxiliary;

C. or the catalyst is prepared by synthesizing Fe$_3$O$_4$ through a coprecipitation method and adding the auxiliary through an immersion method, comprising the following steps:

(1) mixing soluble Fe (II) salt and soluble Fe (III) salt to form a salt solution to form a salt solution in accordance with a catalyst composition ratio, the concentration of Fe (III) in the salt solution being 0.02-0.8 mol/L; adding HCl solution with a concentration of 3-12.1 mol/L; regulating a pH value to 0-3, wherein the molar ratio of Fe(III) to Fe(II) in the salt solution is 2:(0.8-2.8);

(2) adding the aqueous alkali in A method to (1); gradually regulating the pH value of the solution to 0-3 until the alkaline pH value is 9-12; after completing dripping, ageing for 1-10 h, wherein (3) after completing the reaction, separating deposited products from (2) through magnetic field absorption, centrifugal or sucking filtration method; adequately washing the deposited products with deionized water, and drying, to prepare the active component Fe$_3$O$_4$;

(4) combining the auxiliary salt with the active component through the immersion method to form a catalyst, specifically: computing the amount of theoretically required auxiliary salt according to the required auxiliary content to prepare an aqueous solution of the auxiliary salt; immersing equal volume of Fe$_3$O$_4$ obtained in preparation of (3) into the solution; stirring, standing, drying and roasting at a roasting temperature of 200-600° C. for a roasting time of 2-10 h, to prepare the iron-based catalyst containing the auxiliary.

During modification of the molecular sieve, the metal component can be supported to the molecular sieve through one of the following two methods:

(1) preparing through an isometric immersion method, specifically: computing the amount of theoretically required metal salt according to the required metal content to prepare an aqueous solution of the metal salt, wherein the metal salt is selected from: any one or more than two of nitrate, chlorid, bromide, acetate, acetylacetonate, citrate, oxalate and benzoate; immersing equal volume of molecular sieve that needs modification treatment into the solution; stirring, standing, drying and roasting at a roasting temperature of 300-700° C. for a roasting time of 2-10 h, to prepare a metal modified molecular sieve;

(2) preparing through an ion exchange method, specifically: computing the amount of theoretically required metal salt according to the required metal content to prepare an aqueous solution of the metal salt, wherein the metal salt is selected from: any one or more than two of nitrate, chlorid, bromide, acetate, acetylacetonate, citrate, oxalate and benzoate; mixing the molecular sieve that needs modification treatment with a mass ratio of solid to liquid of 1:(10-200); conducting ion exchange for 2-24 h; and washing, drying and roasting at a roasting temperature of 300-700° C. for a roasting time of 2-10 h, to prepare a metal modified molecular sieve.

Two components of a multi-functional composite catalyst can be mixed through one of the following two modes:

(1) particle mixing mode: respectively weighing iron-based catalyst and molecular sieve catalyst powder; respectively tabletting, shaping and screening; and uniformly mixing particles according to a required mass ratio to form a composite catalyst;

(2) layered packing mode: successively packing required mass of the iron-based catalyst and the molecular sieve catalyst on catalyst bed layers in a top-to-bottom sequence of reactors, wherein two catalyst bed layer components contain or do not contain an isolation layer of inert material, and the mass ratio of the isolation layer of inert material to the active component of the composite catalyst is 0.01-10.

When aromatic hydrocarbon is prepared with carbon dioxide hydrogenation, catalyst performance is evaluated through the following manner: placing the prepared composite catalyst into a constant temperature section of a fixed bed reactor, and then reducing the catalyst at $H_2$ atmosphere at 300-400° C., wherein the $H_2$ flow is 10-50 mL/min. After reduction is ended, the temperature is adjusted to reaction temperature, and reducing gas is cut into reaction gas. The reaction products are introduced in a gaseous form into chromatogram for on-line analysis. CO, $N_2$, $CH_4$ and $CO_2$ passes TCD detection, and hydrocarbon and oxygen containing compounds pass FID detection.

The present invention is applied to gas containing the carbon dioxide. The gas refers to any one or more than two of industrial waste gas containing the carbon dioxide, automobile exhaust, coal waste gas, atmosphere and the carbon dioxide absorbed in seawater.

The present invention has the following characteristics:

(1) The catalyst used by the present invention is simple in preparation method, cheap and easy to get in raw material, high in mechanical strength, good in stability, applicable to a fixed bed, a fluidized bed and a slurry reactor, and also applicable to large-scale industrial production.

(2) The present invention can directly obtain the aromatic hydrocarbon products through a one-step method. The prepared aromatic hydrocarbon products mainly include high value added products such as toluene, ethybenzene, xylene, methyl ethylbenzene, trimethyl benzene, dimethyl ethybenzene, etc.

(3) The present invention directly prepares aromatic hydrocarbon through the one-step method, and is simple in reaction apparatus, short in process flow, low in equipment investment and low in energy consumption.

(4) The present invention uses carbon dioxide (greenhouse gas) as carbon resources, which is conducive to realizing cyclic utilization of the carbon resources, reducing dependence on fossil energy and also alleviating environment burden.

DESCRIPTION OF PREFERRED EMBODIMENTS

The technical details of the present invention are described in detail through the following embodiments. It should be indicated that listed embodiments are only used to further illustrate technical features of the present invention, not to limit the present invention.

Embodiment 1

Steps: mixing 15.81 g of $FeCl_3.6H_2O$ and 6.27 g of $FeCl_2.4H_2O$ with 80 mL of water to form a malysite solution, and adding 3.5 mL of 9.0 mol/L HCl solution; under stirring at 60° C., adding about 180 mL of 1.5 mol/L NaOH solution at uniform speed; within about 1.5 h, adjusting the pH value of the solution to about 10; after completing dripping, keeping the temperature and continuing to stir for 1 h, and finally cooling to room temperature; after completing the reaction, separating deposited products through magnetic field absorption; washing the deposited products once with 400 mL of deionized water, and drying at 60° C., to prepare a Na—$Fe_3O_4$ catalyst sample which can be used later after ground, tableted and screened.

Respectively roasting HMCM-22 ($SiO_2/Al_2O_3$=30) purchased from Molecular Sieve Plant of Nankai University, HZSM-5 molecular sieves with silica alumina ratios $SiO_2/Al_2O_3$ of 27, 50, 150 and 300 and HZSM-23 ($SiO_2/Al_2O_3$=80) molecular sieve synthesized by the laboratory for 4 h at 500° C., and grinding, tabletting and screening the samples for later use.

Weighing the above prepared 0.5 g Na—$Fe_3O_4$ catalyst particles and uniformly mixing with 0.5 g HMCM-22, HZSM-5 and HZSM-23 molecular sieve particles for use in evaluation of $CO_2$ hydrogenation reaction in a fixed bed reactor.

Reducing Conditions:

Normal pressure, pure $H_2$ (25 mL/min), 350° C. and reduction time of 8 h. Reaction conditions: $H_2/CO_2$=3.0, a temperature of 320° C., a pressure of 3.0 MPa, and an hourly space velocity of 4000 mL/(h·$g_{cat}$). The influence of the molecular sieve type on $CO_2$ hydrogenation performance of the Na—$Fe_3O_4$/zeolite catalyst is inspected. The result (see Table 1 and Table 2) indicates that, compared with an individual iron-based catalyst, after the molecular sieve is added as the second component to mix with the iron-based catalyst, the $C_{5+}$ content in the hydrocarbon product and aromatic hydrocarbon content in $C_{5+}$ are greatly increased. ZSM-5 molecular sieve has a three-dimensional ten-membered ring porous channel matched with the molecular dimension of aromatic hydrocarbons and appropriate acid strength, and thus has excellent aromatization performance.

TABLE 1

Influence of Molecular Sieve Type on $CO_2$ Hydrogenation Performance of Na—$Fe_3O_4$/Zeolite Composite Catalyst

| Molecular Sieve | Conversion Rate $CO_2$ (%) | Selectivity CO (%) | Hydrocarbon Distribution (C-mol %) | | | Aromatic Hydrocarbon Content in $C_{5+}$ (C-mol %) |
|---|---|---|---|---|---|---|
| | | | $CH_4$ | $C_2$~$C_4$ | $C_{5+}$ | |
| —[a] | 33.7 | 14.3 | 11.7 | 48.4 | 39.9 | 1.0 |
| HZSM-23 | 33.7 | 14.7 | 10.6 | 37.8 | 51.6 | 20.0 |
| HMCM-22 | 34.8 | 13.4 | 11.0 | 31.3 | 57.7 | 31.0 |
| HZSM-5 (300) | 33.0 | 15.0 | 8.6 | 23.2 | 68.2 | 41.0 |
| HZSM-5 (150) | 33.6 | 15.0 | 7.9 | 18.4 | 73.7 | 56.1 |

TABLE 1-continued

Influence of Molecular Sieve Type on CO$_2$ Hydrogenation Performance of Na—Fe$_3$O$_4$/Zeolite Composite Catalyst

| Molecular Sieve | Conversion Rate CO$_2$ (%) | Selectivity CO (%) | Hydrocarbon Distribution (C-mol %) CH$_4$ | C$_2$~C$_4$ | C$_{5+}$ | Aromatic Hydrocarbon Content in C$_{5+}$ (C-mol %) |
|---|---|---|---|---|---|---|
| HZSM-5 (50) | 33.3 | 14.7 | 7.4 | 23.9 | 68.7 | 61.0 |
| HZSM-5 (27) | 33.6 | 13.9 | 7.3 | 24.5 | 68.1 | 63.1 |

$^a$Packing Na—Fe$_3$O$_4$ catalyst only, not packing molecular sieve.

TABLE 2

Aromatic Hydrocarbon Distribution of CO$_2$ Hydrogenation Reaction Products on Na—Fe$_3$O$_4$/Zeolite Composite Catalyst

| Aromatic Hydrocarbon | Aromatic Hydrocarbon | HMCM-22 | HZSM-5(300) | HZSM-5(150) | HZSM-5(27) |
|---|---|---|---|---|---|
| C$_6$ | Benzene | 0.6 | 0.5 | 0.9 | 2.3 |
| C$_7$ | Toluene | 3.8 | 4.9 | 8.5 | 18.7 |
| C$_8$ | Ethylbenzene | 1.7 | 2.4 | 3.1 | 4.6 |
|  | Xylene | 19.0 | 21.8 | 25.3 | 34.2 |
| C$_9$ | Propylbenzene | 1.4 | 1.3 | 0.8 | 0.3 |
|  | Methyl Ethylbenzene | 8.7 | 23.8 | 22.8 | 17.4 |
|  | Trimethylbenzene | 22.1 | 12.3 | 13.5 | 5.5 |
| C$_{10}$ | Diethylbenzene | 2.3 | 4.6 | 2.9 | 1.4 |
|  | Monomethyl Propylbenzene | 5.4 | 5.1 | 2.4 | 1.1 |
|  | Dimethyl Ethybenzene | 9.0 | 11.6 | 11.9 | 4.1 |
|  | Tetramethylbenzene | 10.2 | 1.0 | 1.2 | 0.2 |
| C$_{11}$ | — | 11.4 | 7.3 | 5.3 | 2.7 |
| C$_{12+}$ | — | 4.3 | 3.2 | 1.5 | 7.6 |

Embodiment 2

Steps: respectively weighing the Na—Fe$_3$O$_4$ catalyst and HZSM-5 (SiO$_2$/Al$_2$O$_3$=150) molecular sieve prepared through the method of embodiment 1 in accordance with different mass ratios to form a particle mixed catalyst with a total mass of 1.0 g; and uniformly mixing for use in CO$_2$ hydrogenation reaction. Reducing conditions: Normal pressure, pure H$_2$ (25 mL/min), 350° C. and reduction time of 8 h.

Reaction conditions: H$_2$/CO$_2$=3.0, a temperature of 320° C., a pressure of 3.0 MPa, and an hourly space velocity of 4000 mL/(h·g$_{cat}$). The influence of the mass ratio of the two components on CO$_2$ hydrogenation performance of the Na—Fe$_3$O$_4$/HZSM-5 catalyst is inspected. The result (see Table 3) indicates that, the composite catalyst has double functions, and the two components have synergy. As the two components are changed in scale, when the ratio of the two components Fe/ZSM is 1:1, the performance of the composite catalyst is best and the aromatic hydrocarbon selectivity is highest.

TABLE 3

Influence of Mass Ratio of Two Components on CO$_2$ Hydrogenation Performance of Na—Fe$_3$O$_4$/HZSM-5 (150) Composite Catalyst

| Fe/ZSM (wt/wt) | Conversion Rate CO$_2$ (%) | Selectivity CO (%) | Hydrocarbon Distribution (C-mol %) CH$_4$ | C$_2$~C$_4$ | C$_{5+}$ | Aromatic Hydrocarbon Content in C$_{5+}$ (C-mol %) |
|---|---|---|---|---|---|---|
| 1:7 | 29.0 | 19.4 | 6.7 | 22.9 | 69.4 | 49.9 |
| 1:3 | 32.9 | 15.4 | 7.1 | 20.6 | 72.3 | 54.3 |
| 1:1 | 33.6 | 15.2 | 7.9 | 18.4 | 73.7 | 56.1 |
| 3:1 | 35.0 | 14.5 | 9.2 | 20.4 | 70.4 | 51.3 |
| 7:1 | 35.8 | 14.0 | 10.0 | 24.0 | 66.0 | 46.8 |

Embodiment 3

Steps: respectively weighing 0.5 g of Na—Fe$_3$O$_4$ catalyst prepared through the method in embodiment 1 and 0.5 g of HZSM-5 (SiO$_2$/Al$_2$O$_3$=150) molecular sieve; uniformly mixing particles for use in CO$_2$ hydrogenation reaction. Reducing conditions: Normal pressure, pure H$_2$ (25 mL/min), 350° C. and reduction time of 8 h. Reaction conditions: H$_2$/CO$_2$=3.0, a temperature of 280-380° C., a pressure of 3.0 MPa, and an hourly space velocity of 2000 mL/(h·g$_{cat}$). The influence of the reaction temperature on CO$_2$ hydrogenation performance of the Na—Fe$_3$O$_4$/HZSM-5 catalyst is inspected. The result (see Table 4) indicates that, as the reaction temperature is increased, the CO$_2$ conversion rate is gradually increased, and the C$_{5+}$ selectivity is increased and then decreased. The catalyst always presents excellent CO$_2$ aromatization performance within an inspected temperature range.

TABLE 4

Influence of Reaction Temperature on CO$_2$ Hydrogenation Performance of Na—Fe$_3$O$_4$/HZSM-5 (150) Composite Catalyst

| Reaction Temperature (° C.) | Conversion Rate CO$_2$ (%) | Selectivity CO (%) | Hydrocarbon Distribution (C-mol %) | | | Aromatic Hydrocarbon Content in C$_{5+}$ (C-mol %) |
|---|---|---|---|---|---|---|
| | | | CH$_4$ | C$_2$~C$_4$ | C$_{5+}$ | |
| 280 | 25.2 | 14.3 | 9.8 | 22.1 | 68.1 | 41.2 |
| 300 | 34.5 | 9.1 | 8.7 | 22.0 | 69.3 | 48.0 |
| 320 | 40.1 | 8.2 | 8.0 | 21.6 | 70.4 | 54.0 |
| 340 | 44.1 | 9.2 | 8.6 | 25.1 | 66.3 | 54.3 |
| 360 | 46.3 | 10.5 | 9.2 | 27.1 | 63.7 | 54.7 |
| 380 | 48.4 | 11.9 | 12.0 | 30.3 | 57.7 | 54.3 |

Embodiment 4

Steps: respectively weighing 0.5 g of Na—Fe$_3$O$_4$ catalyst prepared through the method in embodiment 1 and 0.5 g of HZSM-5 (SiO$_2$/Al$_2$O$_3$=150) molecular sieve; uniformly mixing particles for use in CO$_2$ hydrogenation reaction. Reducing conditions: Normal pressure, pure H$_2$ (25 mL/min), 350° C. and reduction time of 8 h. Reaction conditions: H$_2$/CO$_2$=3.0, a temperature of 320° C., a pressure of 1.0-5.0 MPa, and an hourly space velocity of 2000 mL/(h·g$_{cat}$). The influence of the reaction pressure on CO$_2$ hydrogenation performance of the Na—Fe$_3$O$_4$/HZSM-5 catalyst is inspected. The result (see Table 5) indicates that, as the reaction pressure is increased, the CO$_2$ conversion rate is gradually increased, and the CO selectivity is gradually decreased. The C$_{5+}$ selectivity is increased and then decreased. The catalyst always presents excellent CO$_2$ aromatization performance within an inspected pressure range.

TABLE 5

Influence of Reaction Pressure on CO$_2$ Hydrogenation Performance of Na—Fe$_3$O$_4$/HZSM-5 (150) Composite Catalyst

| Reaction Pressure (MPa) | Conversion Rate CO$_2$ (%) | Selectivity CO (%) | Hydrocarbon Distribution (C-mol %) | | | Aromatic Hydrocarbon Content in C$_{5+}$ (C-mol %) |
|---|---|---|---|---|---|---|
| | | | CH$_4$ | C$_2$~C$_4$ | C$_{5+}$ | |
| 1.0 | 31.2 | 24.3 | 8.9 | 28.4 | 62.7 | 46.0 |
| 2.0 | 33.8 | 16.5 | 9.5 | 24.4 | 66.1 | 50.1 |
| 3.0 | 38.6 | 10.4 | 8.5 | 21.0 | 70.5 | 54.0 |
| 4.0 | 40.7 | 8.0 | 10.4 | 22.9 | 66.7 | 46.7 |
| 5.0 | 42.2 | 7.1 | 12.7 | 24.8 | 62.5 | 45.1 |

Embodiment 5

Steps: respectively weighing 0.5 g of Na—Fe$_3$O$_4$ catalyst prepared through the method in embodiment 1 and 0.5 g of HZSM-5 (SiO$_2$/Al$_2$O$_3$=150) molecular sieve; uniformly mixing particles for use in CO$_2$ hydrogenation reaction. Reducing conditions: Normal pressure, pure H$_2$ (25 mL/min), 350° C. and reduction time of 8 h. Reaction conditions: H$_2$/CO$_2$=3.0, a temperature of 320° C., a pressure of 3.0 MPa, and an hourly space velocity of 1000-10000 mL/(h·g$_{cat}$). The influence of the feedstock gas hourly space velocity on CO$_2$ hydrogenation performance of the Na—Fe$_3$O$_4$/HZSM-5 catalyst is inspected. The result (see Table 6) indicates that, as the feedstock gas hourly space velocity is increased, the CO$_2$ conversion rate is gradually decreased, and the C$_{5+}$ selectivity is increased and then decreased, and is maximum when the hourly space velocity is 4000 mL/(h·g$_{cat}$). The catalyst always presents excellent CO$_2$ aromatization performance at the hourly space velocity of 10000 mL/(h·g$_{cat}$).

TABLE 6

Influence of Feedstock Gas Hourly Space Velocity on $CO_2$
Hydrogenation Performance of Na—$Fe_3O_4$/HZSM-5 (150) Composite Catalyst

| Hourly space velocity (mL · g − 1 · h − 1) | Conversion Rate $CO_2$ (%) | Selectivity CO (%) | Hydrocarbon Distribution (C-mol %) | | | Aromatic Hydrocarbon Content in $C_{5+}$ (C-mol %) |
|---|---|---|---|---|---|---|
| | | | $CH_4$ | $C_2$~$C_4$ | $C_{5+}$ | |
| 1000 | 43.1 | 9.4 | 10.5 | 25.4 | 64.1 | 51.5 |
| 2000 | 37.2 | 11.2 | 8.3 | 21.3 | 70.4 | 54.0 |
| 4000 | 33.2 | 17.0 | 7.8 | 19.0 | 73.3 | 56.1 |
| 6000 | 31.7 | 19.0 | 8.0 | 20.2 | 71.9 | 54.0 |
| 8000 | 30.3 | 22.3 | 8.2 | 20.6 | 71.2 | 49.2 |
| 10000 | 28.7 | 25.0 | 10.5 | 24.2 | 65.3 | 47.0 |

Embodiment 6

Steps: respectively weighing 0.5 g of Na—$Fe_3O_4$ catalyst prepared through the method in embodiment 1 and 0.5 g of HZSM-5 ($SiO_2$/$Al_2O_3$=150) molecular sieve; uniformly mixing particles for use in $CO_2$ hydrogenation reaction. Reducing conditions: Normal pressure, pure $H_2$ (25 mL/min), 350° C. and reduction time of 8 h. Reaction conditions: $H_2$/$CO_2$=1.0-6.0, a temperature of 320° C., a pressure of 3.0 MPa, and an hourly space velocity of 2000 mL/(h·$g_{cat}$). The influence of the hydrogen-carbon ratio of the feedstock gas on $CO_2$ hydrogenation performance of the Na—$Fe_3O_4$/HZSM-5 catalyst is inspected. The result (see Table 7) indicates that, as the hydrogen-carbon ratio of the feedstock gas is increased, the $CO_2$ conversion rate is obviously increased. The aromatic hydrocarbon content in $C_{5+}$ always keeps higher value within the inspected hydrogen-carbon ratio range.

TABLE 7

Influence of Hydrogen-Carbon Ratio of Feedstock Gas on $CO_2$
Hydrogenation Performance of Na—$Fe_3O_4$/HZSM-5 (150)
Composite Catalyst

| Hydrogen-Carbon Ratio $H_2$/$CO_2$ | Conversion Rate $CO_2$ (%) | Selectivity CO (%) | Hydrocarbon Distribution (C-mol %) | | | Aromatic Hydrocarbon Content in $C_{5+}$ (C-mol %) |
|---|---|---|---|---|---|---|
| | | | $CH_4$ | $C_2$~$C_4$ | $C_{5+}$ | |
| 1.0 | 22.0 | 17.6 | 4.3 | 19.5 | 76.2 | 60.5 |
| 2.0 | 27.1 | 16.5 | 6.5 | 20.3 | 73.3 | 57.9 |
| 3.0 | 36.0 | 13.1 | 8.6 | 20.8 | 70.7 | 54.0 |
| 4.0 | 45.0 | 9.7 | 10.5 | 21.3 | 68.2 | 53.0 |
| 5.0 | 53.1 | 7.4 | 11.5 | 21.4 | 67.1 | 52.1 |
| 6.0 | 59.5 | 5.7 | 12.9 | 22.2 | 64.9 | 51.2 |

Embodiment 7

Steps: weighing 0.72 g of Ga($NO_3$)3.9$H_2O$, adding about 7.2 mL of deionized water to prepare Ga($NO_3$)$_3$ solution, then weighing 6.0 g of HZSM-5 ($SiO_2$/$Al_2O_3$=150) molecular sieve and immersing equal volume of the molecular sieve in the above Ga($NO_3$)$_3$ solution, stirring, standing for 12 h, drying at 60° C., roasting for 4 h at 500° C. and finally grinding, tabletting and screening for later use. Other metal modified molecular sieves are prepared by the similar method.

Steps: weighing 0.5 g of Na—$Fe_3O_4$ catalyst prepared through the method in embodiment 1 and 0.5 g of 2% M/ZSM-5 molecular sieve prepared; uniformly mixing particles for use in $CO_2$ hydrogenation reaction. Reducing conditions: Normal pressure, pure $H_2$ (25 mL/min), 350° C. and reduction time of 8 h. Reaction conditions: $H_2$/$CO_2$=3.0, a temperature of 320° C., a pressure of 3.0 MPa, and an hourly space velocity of 4000 mL/(h·$g_{cat}$). The influence of different metal modification on $CO_2$ hydrogenation performance of the Na—$Fe_3O_4$/M-ZSM-5 catalyst is inspected. The result (see Table 8 and Table 9) indicates that, the influence of different metal modified molecular sieves on $CO_2$ conversion rate is low, but after metal modification, product compositions are obviously changed and $C_{5+}$ selectivity is reduced to different degrees.

TABLE 8

Influence of Metal Modification on $CO_2$ Hydrogenation
Performance of Na—$Fe_3O_4$/M-ZSM-5 (150) Composite Catalyst

| Metal M | Conversion Rate $CO_2$ (%) | Selectivity CO (%) | Hydrocarbon Distribution (C-mol %) | | | Aromatic Hydrocarbon Content in $C_{5+}$ (C-mol %) |
|---|---|---|---|---|---|---|
| | | | $CH_4$ | $C_2$~$C_4$ | $C_{5+}$ | |
| —[a] | 33.6 | 15.2 | 7.9 | 18.4 | 73.7 | 56.1 |
| Mo | 33.6 | 16.8 | 7.9 | 18.8 | 73.3 | 55.8 |
| Ga | 35.6 | 14.0 | 7.9 | 20.2 | 71.9 | 55.2 |
| Cr | 35.0 | 14.3 | 8.4 | 20.5 | 71.1 | 48.9 |
| La | 35.7 | 13.8 | 8.6 | 20.7 | 70.7 | 48.0 |
| Cu | 35.9 | 13.6 | 8.1 | 24.1 | 67.8 | 47.9 |
| Zn | 35.0 | 13.9 | 8.6 | 22.8 | 68.5 | 41.9 |

[a]Unmodified molecular sieve.

TABLE 9

Aromatic Hydrocarbon Distribution of $CO_2$ Hydrogenation
Reaction Products on Na—$Fe_3O_4$/M-ZSM-5 (150)
Composite Catalyst

| Aromatic Hydrocarbon | — | Mo | Ga | Cr | La | Cu | Zn |
|---|---|---|---|---|---|---|---|
| $C_6$ | 0.9 | 0.8 | 1.1 | 0.7 | 0.7 | 0.9 | 0.5 |
| $C_7$ | 8.5 | 8.6 | 10.4 | 7.6 | 7.2 | 9.1 | 5.6 |
| $C_8$ | 28.4 | 28.3 | 30.8 | 29.2 | 29.5 | 31.1 | 23.5 |
| $C_9$ | 37.0 | 36.8 | 35.1 | 38.1 | 39.3 | 37.1 | 36.4 |
| $C_{10}$ | 18.4 | 17.9 | 15.2 | 19.3 | 19.4 | 17.1 | 25.4 |
| $C_{11}$ | 5.3 | 5.5 | 3.0 | 4.7 | 3.7 | 4.2 | 7.2 |
| $C_{12+}$ | 1.5 | 2.1 | 4.5 | 0.5 | 0.3 | 0.5 | 1.4 |

In the method, $CO_2$ conversion per pass may be above 33%, the hydrocarbon product selectivity may be controlled to be above 80%, the methane content is lower than 8%, $C_{5+}$ hydrocarbon content is higher than 65% and the proportion of the aromatic hydrocarbon in $C_{5+}$ hydrocarbon may be above 63%. The present invention develops a new route for producing aromatic hydrocarbon from carbon dioxide.

We claim:

1. A method for preparing aromatic hydrocarbon with carbon dioxide hydrogenation comprising: directly converting a mixed gas which comprises carbon dioxide and hydrogen, used as feed gas, with the catalysis of a composite catalyst to produce aromatic hydrocarbons, wherein the composite catalyst is a mixture of a first component and a second component, the first component is an iron-based catalyst for making low-carbon olefin via carbon dioxide hydrogenation, and the second component is at least one of metal modified or non-modified molecular sieves which are mainly used for olefin aromatization; and the mass ratio of the first component to the second component is 1:10-10:1;

the iron-based catalyst comprises one or more of FeO, $Fe_2O_3$ and $Fe_3O_4$ as at least one main active component and optionally an auxiliary;

the iron-based catalyst has reverse water gas conversion function and olefin production function with CO hydrogenation;

the auxiliary is an oxide, and the content of the auxiliary is 0-20% of the total mass of the iron-based catalyst; and the second component is a molecular sieve containing ten-membered ring porous structure.

2. The method according to claim 1 wherein the iron-based catalyst comprises $Fe_3O_4$ as an active component, and the method comprises one of the following processes to make the iron-based catalyst:

A. the catalyst is prepared by a one-step synthesis method which comprises the following steps:

(1) mixing soluble Fe (II) salt and soluble Fe (III) salt to form a salt solution or mixing soluble Fe (II) salt, soluble Fe (III) salt and auxiliary salt to form a salt solution in accordance with a catalyst composition ratio, the concentration of Fe (III) in the salt solution being 0.02-0.8 mol/L; adding HCl solution with a concentration of 3-12.1 mol/L; regulating a pH value to 0-3, wherein the molar ratio of Fe(III) to Fe(II) in the salt solution is 2:(0.8-2.8); wherein the soluble Fe (II) salt and the soluble Fe (III) salt are water-soluble salt compounds; and the auxiliary salt is a water-soluble salt compound;

(2) adding aqueous alkali to (1); gradually regulating the pH value of the solution to 0-3 until the alkaline pH value is 9-12; after completing dripping, ageing for 1-10 h, wherein the aqueous alkali is an alkali solution with an adjustable pH value; the concentration of the aqueous alkali is 0.1-8 mol/L, wherein R refers to an organo-functional group and comprises $C_1$-$C_{20}$ alkyl, $C_1$-$C_{20}$ alkenyl or $C_6$-$C_{20}$ aryl;

(3) after completing the reaction, separating deposited products from (2) through magnetic field absorption, centrifugal or sucking filtration method; adequately washing the deposited products with deionized water, drying, optionally roasting at a roasting temperature of 200-600° C. for a roasting time of 2-10 h, to prepare the iron-based catalyst containing the auxiliary;

B. or the catalyst is prepared by a one-step synthesis method which comprises the following steps:

(1) mixing soluble Fe (II) salt and soluble Fe (III) salt to form a salt solution in accordance with a catalyst composition ratio, the concentration of Fe (III) in the salt solution being 0.02-0.8 mol/L; adding HCl solution with a concentration of 3-12.1 mol/L; and regulating a pH value to 0-3, wherein the molar ratio of Fe(III) to Fe(II) in the salt solution is 2:(0.8-2.8);

(2) adding aqueous alkali containing Na or K in A method to (1); gradually regulating the pH value of the solution to 0-3 until the alkaline pH value is 9-12; and after completing dripping, ageing for 1-10 h;

(3) after completing the reaction, separating deposited products from (2) through magnetic field absorption, centrifugal or sucking filtration method; washing the deposited products with deionized water; controlling the content of remaining Na or K in the catalyst by controlling washing times and water consumption per washing; drying, roasting or not roasting at a roasting temperature of 200-600° C. for a roasting time of 2-10 h, to prepare the iron-based catalyst containing the auxiliary;

C. or the catalyst is prepared by synthesizing $Fe_3O_4$ through a coprecipitation method and adding the auxiliary through an immersion method, comprising the following steps:

(1) mixing soluble Fe (II) salt and soluble Fe (III) salt to form a salt solution in accordance with a catalyst composition ratio, the concentration of Fe (III) in the salt solution being 0.02-0.8 mol/L; adding HCl solution with a concentration of 3-12.1 mol/L; and regulating a pH value to 0-3, wherein the molar ratio of Fe(III) to Fe(II) in the salt solution is 2:(0.8-2.8);

(2) adding the aqueous alkali in A method to (1); gradually regulating the pH value of the solution to 0-3 until the alkaline pH value is 9-12; and after completing dripping, ageing for 1-10 h;

(3) after completing the reaction, separating deposited products from (2) through magnetic field absorption, centrifugal or sucking filtration method; adequately washing the deposited products with deionized water, and drying, to prepare the active component $Fe_3O_4$;

(4) combining the auxiliary salt with the active component through the immersion method to form a catalyst, which comprises: computing the amount of theoretically required auxiliary salt according to the required auxiliary content to prepare an aqueous solution of the auxiliary salt; immersing equal volume of $Fe_3O_4$ obtained in preparation of (3) into the solution; stirring, standing, drying and roasting at a roasting temperature of 200-600° C. for a roasting time of 2-10 h, to prepare the iron-based catalyst containing the auxiliary.

3. The method according to claim 1, wherein during modification of the molecular sieve, the metal component is supported by the molecular sieve through one of the following two methods:

(1) preparing through an isometric immersion method, which comprises: computing the amount of theoretically required metal salt according to the required metal content to prepare an aqueous solution of the metal salt, wherein the metal salt is selected from the group consisting of: nitrate, chloride, bromide, acetate, acetylacetonate, citrate, oxalate and benzoate; immersing equal volume of molecular sieve that needs modification treatment into the solution; stirring, standing, drying and roasting at a roasting temperature of 300-700° C. for a roasting time of 2-10 h, to prepare a metal modified molecular sieve;

(2) preparing through an ion exchange method, which comprises: computing the amount of theoretically required metal salt according to the required metal content to prepare an aqueous solution of the metal salt, wherein the metal salt is selected from the group consisting of: nitrate, chloride, bromide, acetate, acetylacetonate, citrate, oxalate and benzoate; mixing the molecular sieve that needs modification treatment with a mass ratio of solid to liquid of 1:(10-200); conducting ion exchange for 2-24 h; and washing, drying and roasting at a roasting temperature of 300-700° C. for a roasting time of 2-10 h, to prepare a metal modified molecular sieve.

4. The method according to claim 1 comprising mixing the two components of the composite catalyst through one of the following two modes:
   (1) particle mixing mode: respectively weighing iron-based catalyst and molecular sieve catalyst powder; respectively tableting, shaping and screening; and uniformly mixing particles according to a required mass ratio to form a composite catalyst;
   (2) layered packing mode: successively packing required mass of the iron-based catalyst and the molecular sieve catalyst on catalyst bed layers in a top-to-bottom sequence of reactors, wherein two catalyst bed layer components contain or do not contain an isolation layer of inert material, and the mass ratio of the isolation layer of inert material to the active component of the composite catalyst is 0.01-10.

5. The method according to claim 1, wherein the reaction temperature is 250-450° C.; the reaction pressure is 0.01-10.0 MPa; feedstock gas hourly space velocity is 500-50000 mL/(h·gcat) and $H_2/CO_2$ molar ratio in the feed gas is 0.5-8.0.

6. The method according to claim 1, wherein the carbon dioxide is present in at least one of industrial waste gas, automobile exhaust, coal waste gas, atmosphere and seawater.

7. The method of claim 1 wherein the mass ratio of the first component to the second component is 1:3-3:1.

8. The method of claim 1 wherein the iron-based catalyst comprises $Fe_3O_4$ as the main active component.

9. The method of claim 1 wherein the content of the auxiliary in the iron-based catalyst is 0.5-10% of the total mass of the iron-based catalyst.

10. The method of claim 1 wherein the second component is at least one of ZSM-5, ZSM-22, ZSM-23 and MCM-22 molecular sieves.

11. The method of claim 1 wherein the second component is at least one of ZSM-5 and MCM-22 molecular sieves.

12. The method of claim 1 wherein the second component has a silica alumina ratio of 20-200.

13. The method of claim 1 wherein the metal modified molecular sieves comprise at least one metal element selected from the group consisting of Mo, Ga, Cr, La, Cu and Zn in an amount of 0.1%-20% based on the mass of the metal modified molecular sieves.

14. The method of claim 1 wherein the metal modified molecular sieves comprise 0.5%-10% of at least one metal element based on the mass of the metal modified molecular sieves.

15. The method of claim 1 wherein the auxiliary is at least one of K oxide, Na oxide, Cu oxide, Mn oxide, V oxide, Zr oxide, Zn oxide, and Ce oxide.

16. A method for preparing aromatic hydrocarbon with carbon dioxide hydrogenation comprising: directly converting a mixed gas which comprises carbon dioxide and hydrogen, used as feed gas, with the catalysis of a composite catalyst to produce aromatic hydrocarbons,
   wherein the composite catalyst is a mixture of a first component and a second component, the first component is an iron-based catalyst for making low-carbon olefin via carbon dioxide hydrogenation, and the second component is at least one of metal modified or non-modified molecular sieves which are mainly used for olefin aromatization; and the mass ratio of the first component to the second component is 1:10-10:1; and
   the method comprises mixing the two components of the composite catalyst through one of the following two modes:
   (1) particle mixing mode: respectively weighing iron-based catalyst and molecular sieve catalyst powder; respectively tableting, shaping and screening; and uniformly mixing particles according to a required mass ratio to form a composite catalyst;
   (2) layered packing mode: successively packing required mass of the iron-based catalyst and the molecular sieve catalyst on catalyst bed layers in a top-to-bottom sequence of reactors, wherein two catalyst bed layer components contain or do not contain an isolation layer of inert material, and the mass ratio of the isolation layer of inert material to the active component of the composite catalyst is 0.01-10.

* * * * *